United States Patent [19]

McVie et al.

[11] Patent Number: 5,269,951

[45] Date of Patent: Dec. 14, 1993

[54] ORGANOSILICON COMPOUNDS

[75] Inventors: James McVie, Barry; Martin Rowlands, Wales, both of United Kingdom

[73] Assignee: Dow Corning Corporation, Barry, United Kingdom

[21] Appl. No.: 914,303

[22] Filed: Jul. 17, 1992

[30] Foreign Application Priority Data

Jul. 18, 1991 [GB] United Kingdom ................. 9115592

[51] Int. Cl.$^5$ ..................... C07D 303/02; C07F 7/02; C08G 77/04; D60M 15/19
[52] U.S. Cl. ...................................... 252/8.6; 252/89; 252/174.15; 528/38; 549/215
[58] Field of Search .................................. 252/8.6–8.9, 252/174.05; 528/38; 549/215

[56] References Cited

U.S. PATENT DOCUMENTS

| | | | |
|---|---|---|---|
| 2,883,397 | 4/1959 | Bailey | 260/348 |
| 3,219,624 | 11/1965 | Cohen | 260/46.5 |
| 4,876,363 | 10/1989 | Funahashi et al. | 549/215 |
| 5,000,861 | 3/1991 | Yang | 252/8.6 |
| 5,017,297 | 5/1991 | Spyropoulos et al. | 252/8.8 |
| 5,115,069 | 5/1992 | Moteni et al. | 52.8/15 |

FOREIGN PATENT DOCUMENTS

| | | |
|---|---|---|
| 834326 | 5/1960 | United Kingdom . |
| 1140536 | 1/1969 | United Kingdom . |
| 1549180 | 7/1979 | United Kingdom . |

*Primary Examiner*—Christine Skane
*Assistant Examiner*—Michael P. Tierney
*Attorney, Agent, or Firm*—Timothy J. Troy; Robert L. McKellar; Alexander Weitz

[57] ABSTRACT

Organosilicon compounds are disclosed which are multi-functional and possess utility as chain branching agents for aminofunctional polysiloxanes used in the softening of textiles and fabrics. The organosilicon compounds possess epoxy functionality and may have further alkyl functionality and/or polyalkylene oxide functionality.

8 Claims, No Drawings

ORGANOSILICON COMPOUNDS

This invention relates to novel organosilicon compounds having an epoxy group attached to a silicon atom. Compounds according to the invention have utility, for example as chain branching agents for aminofunctional materials.

In many European countries there is growing concern regarding the quantity of surfactant and other materials leached from fabrics and from textile mill effluents and their effect on the environment. Most surfactants by their very nature are water dispersible and, as they form no bond with the fabric or substances thereon, they are easily solubilised when the fabric is washed. One solution is to use functional surfactants capable of forming a chemical bond with either the fabric or a substance thereon.

It is well known in the prior art to employ aminofunctional organosilicon compounds in the treatment of textiles and fabrics for various purposes including the imparting of "softening" benefit to the materials being treated. Descriptions exemplary of such treatment are given for example in British Patent 1 549 180 dated Jul. 25th 1979 and U.S. Pat. No. 5,000,861 dated Mar. 19th 1991. While emulsions containing linear aminofunctional siloxanes are used to impart softness to textiles and fabrics to which they are applied, such treatments suffer from the disadvantage in that there is some lack of prolonged durability of the aminofunctional siloxanes and hence there is not provided the handle characteristics which could be provided by an elastomeric finish. In addition, following application of the emulsion to the textile or fabric, substances from the emulsion, e.g. surfactants, are also free to be removed upon washing and therefore become another component of a chemical effluent requiring disposal.

We have now found that a finish of improved durability may be produced using an emulsion containing linear aminofunctional siloxane and selected organosilicon compounds having an epoxy group attached to a silicon atom.

While epoxy functional organosilicon compounds are not new in the art (see for example British Patents 834 326 dated 4th May 1960 and 1 140 536 dated 22nd January 1969) the prior art does not teach the structure of the polysiloxanes of the present invention.

The invention provides in one of its aspects a compound having the formula

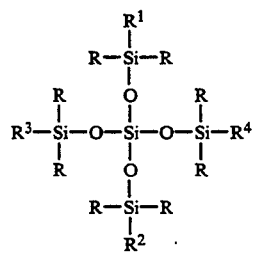

wherein R is an alkyl group having from 1 to 6 carbon atoms, $R^1$ is an epoxy group attached to the silicon atom by a divalent alkylene or alkyleneoxy group and the groups $R^2$, $R^3$, $R^4$ are each $R^1$ or a polyoxyalkylated substituent having oxyethylene and optionally oxypropylene units present in the molecule and having the formula $-(CH_2)_3O(C_2H_4O)_x(C_3H_6O)_yR^5$ in which x and y are each integers having a value up to about fifty and $R^5$ is a group selected from the group consisting of hydrogen, alkyl groups having from one to about six carbon atoms, $-OH$, $-OCH_3$ and $-OCOCCH_3$; with the proviso that $R^4$ may be the group $-(CH_2)_3(CH_2)_zCH_3$ wherein z is an integer having a value of from three to fourteen.

Compounds according to the invention which contain two or more groups $R^1$ are capable of reaction with aminofunctional siloxanes to yield a crosslinked product. Preferred compounds have from about 5 to about 22 weight percent of the epoxy group per molecule. Compounds according to the present invention may be made by a hydrosilylation reaction of the corresponding silane and an unsaturated epoxide, for example allyl glycidyl ether in presence of a hydrosilylation catalyst.

Compounds according to the invention may, and preferably do, also have a polyoxyalkylated substituent and/or an aliphatic group $-(CH_2)_3(CH_2)_zCH_3$ where z has a value from 3 to 14. The polyoxyalkylated substituent confers hydrophilic characteristics to the compound whereas the aliphatic group confers hydrophobic characteristics. Compounds may be prepared which have surfactant characteristics and which can be reacted with, and thus bonded to suitably reactive materials, for example aminofunctional siloxanes.

Thus, compounds according to the present invention offer the advantage in that they possess reactive sites and are capable when added to aminofunctional softening compositions of curing to provide a finish of improved durability. The preferred compounds of this invention react with the amino group of the softener composition and provide a crosslinked network which cannot be washed away.

Individual species of compounds are provided wherein $R^2$, $R^3$ and $R^4$ are each $R^1$, where $R^2$ is $R^1$, $R^3$ is a polyoxyalkylated substituent where the unit x has a value of from 7 to 18 and y is zero and R is the group $-(CH_2)_3(CH_2)_zCH_3$. The compounds have a viscosity of from about fifty to about two thousand centistokes measured at 25° C., ranging upwards to compounds which are waxy materials.

The invention provides in another of its aspects a composition comprising in combination a compound according to the invention and an aminofunctional polysiloxane. The composition may be in the form of an aqueous emulsion and the aminofunctional polysiloxane may be any of those known for use in textile and fabric treating compositions. Preferred aminofunctional polysiloxanes are those according to the general formula

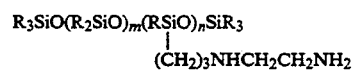

where R is a hydrocarbon group, more preferably an alkyl group having from 1 to 6 carbon atoms, m has a value of 50 to 5000 and D has a value of 1 to 25.

Compositions containing the aminofunctional siloxane and a compound according to the invention may be applied to textiles and induced to react thereon, for example by heating to about 80° to 100° C. preferably in presence of a catalyst.

In order that the invention may become more clear there now follows a description of example materials according to the invention and methods of preparing them. Tables I and II show twelve compounds A to M which were prepared in accordance with the present invention. In Table I, $R^1$, $R^2$, $R^3$ and $R^4$ conform to the groups shown in the above formula. Table II shows some properties of compounds A to M. The examples which follow Tables I and II show how to prepare some of the compounds shown in Tables I and II and use of the compounds as modifiers for aminopolysiloxanes.

TABLE I

| COMPOUND | $R^1$ | $R^2$ | $R^3$ | $R^4$ | SOLUBILITY IN WATER |
|---|---|---|---|---|---|
| A | Epoxy | Epoxy | Epoxy | Epoxy | No |
| B | Epoxy | Epoxy | (EO)7 | C8 | No |
| C | Epoxy | Epoxy | (EO)7 | C12 | No |
| D | Epoxy | Epoxy | (EO)7 | C18 | No |
| E | Epoxy | Epoxy | (EO)12 | C8 | Slight |
| F | Epoxy | Epoxy | (EO)12 | C12 | Slight |
| G | Epoxy | Epoxy | (EO)12 | C18 | No |
| H | Epoxy | Epoxy | (EO)18 | C8 | Yes |
| J | Epoxy | Epoxy | (EO)18 | C12 | Yes |
| K | Epoxy | Epoxy | (EO)18 | C14 | Yes |
| L | Epoxy | Epoxy | (EO)18 | C16 | Yes |
| M | Epoxy | Epoxy | (EO)18 | C18 | Yes |

By the expression "EO" is meant a polyethylene oxide group —$(CH_2)_3(OC_2H_4)_xOH$, x being 7, 12 or 18. By the expressions "C8", "C12", "C14", "C16" and "C18" are meant the alkyl group $(CH_2)_3(CH_2)_zCH_3$ where z is 4, 8, 10, 12 or 14.

TABLE II

| COMPOUND | APPEARANCE (RT)* | VISCOSITY (CS)** | % EPOXY (Wt) |
|---|---|---|---|
| A | Clear Liquid | 50 | 22.4 |
| B | Hazy Liquid | 100 | 8.5 |
| C | Hazy Liquid | 180 | 8.0 |
| D | Hazy Liquid | 200 | 7.4 |
| E | Hazy Liquid | 1000 | 6.9 |
| F | Hazy Liquid | 1750 | 6.6 |
| G | Hazy Liquid | 2000 | 6.2 |
| H | Waxy | — | 5.6 |
| J | Waxy | — | 5.4 |
| K | Waxy | — | 5.1 |
| L | Waxy | — | 5.2 |
| M | Waxy | — | 5.3 |

*(RT) = Room Temperature
**Measured at 25° C.

The multifunctional silicone crosslinking agents may be prepared in accordance with the following schematic:

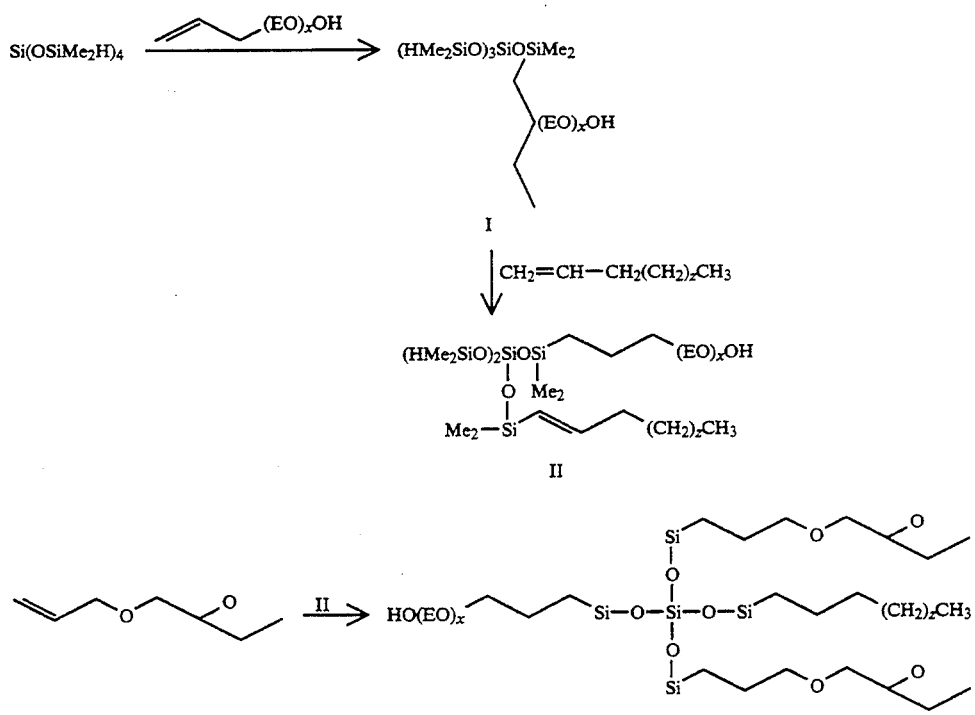

The following examples are set forth for the purpose of illustrating the present invention.

EXAMPLE I

Into a flask equipped for reflux there was added 200g of allyl glycidyl ether, 70 μl of chloroplatinic acid ($H_2PtCl_6$), and 0.2g of sodium acetate (NaOAc). The flask was heated to 120° C. Slowly added to the flask over six hours was 71.8 g of the compound tetrakis(dimethylsiloxy)silane Si(OSiMe$_2$H)$_4$ which is the equilibrated product from the reaction of tetramethyldisiloxane and tetraethoxysilane. Upon completion of the addition of Si(OSiMe$_2$H)$_4$, the reaction was monitored by IR. The reaction proceeded slowly and another 70 μl of the catalyst chloroplatinic acid was added. After twelve hours and following stripping, the product was isolated and identified as the tetraepoxyfunctional siloxane identified as Compound "A" shown above in Tables I and II. The compound has four available epoxide groups which each provide a site for reaction to occur. This compound is useful in fabric treatments for providing increased wash durability of textile and fabric treatments which use aminofunctional organosilicon compounds.

EXAMPLE II

Into a flask equipped with a Dean/Stark apparatus there was added one hundred-fifty grams of allyl polyoxyethylene glycol $CH_2CHCH_2(OCH_2CH_2)_{18}OH$, forty-five grams of toluene and 54.5g of the compound tetrakis(dimethylilane $Si(OSiMe_2H)_4$. The contents were dried using the Dean/Stark apparatus and the flask was cooled to 90° C. To the flask was added 100 μl of chloroplatinic acid ($H_2PtCl_6$) and 0.25g of sodium acetate (NaOAc) and the reaction was refluxed for two hours. The flask was cooled to room temperature. To the flask was added 34.5g of the alkene 1-hexadecene over a period of two hours and the flask was refluxed for another two hours. The flask was again cooled to room temperature. Into a second flask was added 57g of ally glycidyl ether and the second flask was heated to 120 to 130° C. The contents of the first flask were added to the second flask over a period of two hours. An additional ten grams of 1-hexadecene was added to the second flask, the flask was cooled, filtered and when the solvents had been stripped off a product was isolated and identified as Compound "L" which is shown in Tables I and II.

EXAMPLES III–VI

Example II was repeated except that in Example III there was employed 17.3 grams of the alkene 1-octene; in Example IV there was employed 25.9 grams of the alkene 1-decene; in Example V there was employed 30.2 grams of the alkene 1-tetradecene; and in Example VI there was employed 21.6 grams of the alkene 1-decene.

In Tables I and II the compound formed in accordance with the method of Example III is shown as "H". Compound "K" was formed in accordance with the method of Example V and is shown in Tables I and II. The compound formed in accordance with the method of Examples IV and VI is not shown in Tables I and II but the compound was structurally similar to products "H", "K" and "L" except for the number of carbon atoms in the $R^4$ group.

EXAMPLE VII

A three-necked 250ml round-bottomed flask equipped with a pressure equalizing funnel, a condenser, a thermometer and an air driven stirrer, was charged with $Si(OSiMe_2H)_4$ (20g, 0.24 mole SiH), allylpolyether (0.06 mole), sodium acetate (0.1g) and touene (25g). The pressure equalizing funnel was charged with alkene. The mixture was heated to 90° C. and chloroplatinic acid solution (25ml) added. The mixture was heated to 120° C. and after one hour the alkene (0.06 mole) was added dropwise from the funnel. The mixture was held at 120° C. for a further one hour then cooled to ambient temperature.

A second 250ml round bottomed flask equipped with a pressure equalizing funnel, condenser, thermometer and air stirrer, was charged with allylglycidyl ether (20.55g, 0.18 mole) and chloroplatinic acid solution (10ml). The contents of the first flask were transferred to the pressure equalizing funnel on the second flask. The allylglycidyl ether was heated to 120° C. and the contents of the funnel added dropwise to the flask. Once addition was complete the mixture was heated for three hours at 120° C. The flask was cooled to ambient temperature, filtered through a bed of dicalite, the toluene and excess allylglycidyl ether removed under vacuum.

The quantities of allylpolyether and alkene used for each run are given in Table III.

TABLE III

| Run No. | Allyl-polyether | Wt. g | Alkene | Wt. g | Compound |
|---|---|---|---|---|---|
| 12 | A | 22 | Octene | 6.8 | B |
| 13 | A | 22 | Dodecene | 10.2 | C |
| 14 | A | 22 | Octadaene | 15.4 | D |
| 15 | B | 36 | Octene | 6.8 | E |
| 16 | B | 36 | Dodecene | 10.2 | F |
| 17 | B | 36 | Octadecene | 15.4 | G |
| 18 | C | 54 | Octene | 6.8 | H |
| 19 | C | 54 | Dodecene | 10.2 | J |
| 20 | C | 54 | Tetradecene | 11.8 | K |
| 21 | C | 54 | Hexadecene | 13.4 | L |
| 22 | C | 54 | Octadecene | 15.4 | M |

A = $CH_2\!=\!CHCH_2(OCH_2CH_2)_7OH$
B = $CH_2\!=\!CHCH_2(OCH_2CH_2)_{12}OH$
C = $CH_2\!=\!CHCH_2(OCH_2CH_2)_{18}OH$

EXAMPLE VIII

The compounds in Tables I and II were tested as reactive surfactants for amine functional polysiloxanes by preparing an emulsion containing 15 parts of an amine functional polysiloxane, nine parts of the compound of the present invention, 0.25 part of acetic acid and 75.75 parts of water. Each compound was mixed with the amine functional polysiloxane and acetic acid and heated to 80° C. for sixteen hours. The products formed white emulsions which proceeded to form products which varied from soft gels to rubber-like gels, indicating that the compounds of the present invention were capable of functioning as reactive siloxanes rendering them useful in aminosilicone fabric softener emulsion systems. The compounds of the present invention form crosslinked networks with the aminosilicone materials. The amine functional polysiloxanes which were tested in accordance with this example are well known commercially available materials and have the formula:

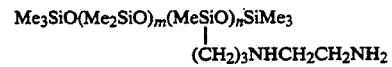

in which Me indicates methyl, m is an integer having a value of 50 to 5000 and D is an integer having a value of to 125. The mole percent of amine of these amine functional polysiloxanes varied from about 0.6 to 2.3.

It should be apparent from the foregoing that many other variations and modifications may be made in the structures, compounds, compositions and methods described herein without departing from the essential features and concepts of the present invention. Accordingly it should be clearly understood that the forms of the invention described herein are exemplary only and are not intended as limitations on the scope of the present invention.

That which is claimed is:

1. A compound having the formula

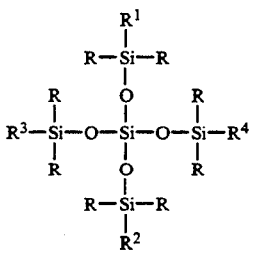

wherein R is an alkyl group having from 1 to 6 carbon atoms, each of $R^1$, $R^2$, $R^3$, and $R^4$ is selected from the group consisting of (a) an epoxy group attached to the silicon atom by a divalent alkylene or alkyleneoxy group, (b) a polyoxyalkylated substituent having the formula $-(CH_2)_3O(C_2H_4O)_x(C_3H_6O)_yR^5$ in which x and y are each integers and each having a value of from 0 to 50, with the proviso that only one of x or y can be zero at any given time, and $R^5$ is a group of selected from the group consisting of hydrogen, alkyl groups having from one to about six carbon atoms, $-OH$, $-OCH_3$, and $-OCOCCH_3$, and (c) a group having the formula $-(CH_2)_3(CH_2)_zCH_3$ wherein z is an integer having a value of from three to fourteen and wherein at least one of $R^1$, $R^2$, $R^3$, and $R^4$ is (a) and at least one of $R^1$, $R^2$, $R^3$, and $R^4$ is (b).

2. The compound of claim 1 in which (a) is

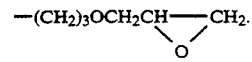

3. The compound of claim 1 wherein the unit x has a value of from 7 to 18 and y is zero.

4. The compound of claim 1 in which one of $R^1$, $R^2$, $R^3$, and $R^4$ is (c).

5. The compound of claim 1 in which the viscosity of the compound is from about fifty to two thousand centistokes measured at 25° C.

6. The compound of claim 1 in which the compound is a waxy material.

7. The compound of claim 1 in which two of $R^1$, $R^2$, $R^3$, and $R^4$ are (a).

8. The compound of claim 2 in which two of $R^1$, $R^2$, $R^3$, and $R^4$ are (a).

* * * * *